(12) United States Patent
Zeng (10) Patent No.: US 7,697,975 B2
(45) Date of Patent: Apr. 13, 2010

(54) METHODS AND APPARATUS FOR FLUORESCENCE IMAGING USING MULTIPLE EXCITATION-EMISSION PAIRS AND SIMULTANEOUS MULTI-CHANNEL IMAGE DETECTION

(75) Inventor: Haishan Zeng, Vancouver (CA)

(73) Assignee: British Colombia Cancer Agency, Vancouver, BC (CA)

( * ) Notice: Subject to any disclaimer, the term of this patent is extended or adjusted under 35 U.S.C. 154(b) by 1487 days.

(21) Appl. No.: 10/453,040

(22) Filed: Jun. 3, 2003

(65) Prior Publication Data

US 2004/0245350 A1    Dec. 9, 2004

(51) Int. Cl.
*A61B 6/00* (2006.01)
(52) U.S. Cl. ............... 600/473; 600/474; 600/475; 600/476; 600/477; 356/301; 356/317; 356/318; 356/319; 356/320
(58) Field of Classification Search ......... 600/473–477, 600/310, 317; 356/301, 317–320
See application file for complete search history.

(56) References Cited

U.S. PATENT DOCUMENTS

| | | | |
|---|---|---|---|
| 4,675,529 A * | 6/1987 | Kushida ............ 250/458.1 |
| 4,852,579 A | 8/1989 | Gilstad et al. |
| 4,884,133 A | 11/1989 | Kanno et al. |
| 5,012,609 A * | 5/1991 | Ignatius et al. ....... 47/1.01 R |
| 5,094,958 A * | 3/1992 | Klainer et al. ......... 436/172 |
| 5,241,170 A * | 8/1993 | Field et al. .......... 250/214 VT |
| 5,507,287 A | 4/1996 | Palcic et al. |
| 5,537,229 A * | 7/1996 | Brandestini et al. ...... 358/509 |
| 5,590,660 A | 1/1997 | MacAulay et al. |
| 5,647,368 A | 7/1997 | Zeng et al. |
| 5,749,830 A | 5/1998 | Kaneko et al. |
| 5,769,792 A | 6/1998 | Palcic et al. |
| 5,827,190 A | 10/1998 | Palcic et al. |
| 5,926,213 A | 7/1999 | Hafele et al. |
| 5,930,424 A | 7/1999 | Heimberger et al. |
| 5,938,617 A | 8/1999 | Vo-Dinh |
| 5,986,271 A | 11/1999 | Lazarev et al. |
| 5,999,844 A | 12/1999 | Gombrich et al. |
| 6,019,719 A | 2/2000 | Schulz et al. |
| 6,025,904 A * | 2/2000 | Kiyonaga et al. ........... 355/41 |
| 6,061,591 A | 5/2000 | Freitag et al. |

(Continued)

FOREIGN PATENT DOCUMENTS

EP        0 736 765 A1    10/1996

(Continued)

OTHER PUBLICATIONS

Wang, "Fluorescence diagnostics and kinetic studies in the head and neck region utilizing low-dose alpha-aminolevulinic acid sensitization", Cancer Letters, v. 135, n. 1, 1999 US.

*Primary Examiner*—Brian Casler
*Assistant Examiner*—John F Ramirez
(74) *Attorney, Agent, or Firm*—Trexler, Bushnell, Giangiorgi, Blackstone & Marr, Ltd.

(57) ABSTRACT

Methods and apparati for fluorescence imaging using multiple excitation-emission pairs is revealed. A target object is illuminated by light in at least two spectral regions, causing fluorescence emission in at least two spectral regions. The emitted light is collected and separated for analysis.

30 Claims, 6 Drawing Sheets

U.S. PATENT DOCUMENTS

| | | | |
|---|---|---|---|
| 6,148,227 | A | 11/2000 | Wagnieres et al. |
| 6,212,425 | B1 | 4/2001 | Irion et al. |
| 6,364,829 | B1 | 4/2002 | Fulghum |
| 6,390,978 | B1 | 5/2002 | Irion et al. |
| 6,414,779 | B1 | 7/2002 | Mandella et al. |
| 6,510,338 | B1 | 1/2003 | Irion et al. |
| 6,537,211 | B1 * | 3/2003 | Wang et al. .................. 600/178 |
| 6,571,118 | B1 * | 5/2003 | Utzinger et al. ............. 600/476 |
| 6,640,131 | B1 | 10/2003 | Irion et al. |
| 2001/0056294 | A1 * | 12/2001 | Hiramoto et al. .............. 607/88 |
| 2002/0103439 | A1 | 8/2002 | Zeng et al. |
| 2002/0105505 | A1 * | 8/2002 | Sendai ....................... 345/204 |
| 2002/0138008 | A1 * | 9/2002 | Tsujita et al. ................ 600/473 |

FOREIGN PATENT DOCUMENTS

| | | |
|---|---|---|
| WO | WO 90/10276 A1 | 9/1990 |
| WO | WO 03/062799 A2 | 7/2003 |

\* cited by examiner

FIGURE 1a

Prior Art

FIGURE 1b

Prior Art

METHODS AND APPARATUS FOR FLUORESCENCE IMAGING USING MULTIPLE EXCITATION-EMISSION PAIRS AND SIMULTANEOUS MULTI-CHANNEL IMAGE DETECTION

BACKGROUND OF THE INVENTION

1. Field of the Invention

Various optical apparati such as microscopes, endoscopes, telescopes, cameras etc. support viewing or analyzing the interaction of light with objects such as planets, plants, rocks, animals, cells, tissue, proteins, DNA, semiconductors, etc. Accordingly, reflected and/or light emitted from the interaction of objects with light, may provide multi-band spectral images yielding useful information related to physical structure (morphological image data) and/or spectral image information related to the chemical make-up, sub-structure and/or other characteristics related to the target object. These light emission images, such as luminescence or fluorescence, may also provide a means to assess endogenous chemicals or exogenous substances such as dyes employed to enhance visualization, drugs, therapeutic intermediaries, or other agents.

In the field of medical imaging and more particularly endoscopy, reflected white light, native tissue autofluorescence, luminescence, chemical emissions, near-IR, and other spectra provide a means to visualize tissue and gather diagnostic information. In addition to visualization of tissue morphology the interaction of light in various parts of the electromagnetic spectrum has been used to collect chemical information. Three general real-time imaging modalities for endoscopy that are of interest include white-light reflectance imaging, fluorescence emission and near infrared imaging modalities.

In endoscopy, conventional white light imaging is typically used to view surface morphology, establish landmarks, and assess the internal organs based on appearance. Applications for viewing the respiratory and gastro-intestinal tracts are well established. Fluorescence imaging has evolved more recently and tissue autofluorescence has been exploited for the detection of early cancer. Similarly, observations of various native and induced chemical interactions, such as labeling tissue with proteins, for example, have been accomplished using fluorescence imaging. Fluorescently-tagged monoclonal antibodies are sometimes used to label specific cellular proteins, which in turn may be detected and/or be measured, optically.

Fluorescence imaging provides a means to detect disease while aiding in the determination of the boundaries that separate diseased from healthy tissue. Accordingly, these methods have been applied to the detection of early cancer in epithelial tissues. Except for the skin, epithelial tissue imaging is usually performed with an endoscope which provides access to the internal surfaces of various body organs such as the respiratory tract (lung) and GI tract. Tissue surfaces are usually not flat, and therefore the light distribution used to illuminate tissue and the light collection efficiency may vary markedly for different image pixels. To compensate for these conditions, and other variables associated with endoscopic imaging, normalization methods are employed to help correct for the geometrical and optical non-uniformities, ideally to make acquired images more diagnostically useful. Typically, this image normalization involves acquiring one image (a sort of reference), best matching (also called aligning or registering) it to a second (diagnostic image) and using the reference image it to correct or process one or more pixels of the diagnostic image. These endoscopic imaging methods are sometimes called two channel or multi-channel imaging. In modern devices, typically the images are acquired and manipulated in the digital domain and may be mixed, matched, colored or otherwise processed prior to presentation on a display device such as a monitor.

"Optical modulator" as used herein means a device or combination of optical and/or electro-optical devices used to alter the wavelength(s), and/or to alter the intensity, and/or to time-gate various spectra of electromagnetic radiation. Various filters, filter wheels, lenses, mirrors, micro-mirror arrays, liquid crystals, or other devices under mechanical or electrical control may be employed alone or in combination to comprise such an optical modulator. Certain embodiments of the present invention utilize two optical modulators, one associated with modulating light source spectrum used to interrogate (illuminate) a target object. A second optical modulator may be used to process the reflected and/or emitted light returned after interacting with the object. In some cases, such as in vivo endoscopic use, interaction of source illumination may be with lung tissue and returned light may include various reflected and re-emitted spectra.

Light in various spectra may be used to advantage. For example, near infrared light may be used to measure tissue oxygenation and may also help visualize or make measurements through blood. These properties may be used, for example, to verify that a biopsy was taken at the correct site. In addition, the present invention discusses, and in combination with existing spectral band imaging, exploits recently discovered tissue fluorescence properties in the near infrared spectral band.

2. Description of the Related Art

U.S. Pat. No. 6,364,829, to Fulghum, entitled, "Autofluorescence imaging system for endoscopy", discusses a broadband light source used to provide both visible light (which induces minimal autofluorescence) and ultraviolet light (capable of inducing tissue autofluorescence). Images are detected, for example, by a single imaging detector located at the distal tip of an endoscope. Electronic means are provided to switch (modulate) the source illumination spectrum used to interact with a target object, such as tissue. Various light sources, filter wheels, shutters, mirrors, dichroic mirrors, spectrum, light sources, intensities and timing diagrams are discussed in this prior art and are therefore included by reference, herein.

U.S. Pat. No. 6,148,227, to Wagnieres, entitled, "Diagnosis apparatus for the picture providing recording of fluorescing biological tissue regions", discusses illumination spectrum and components for fluorescence imaging. In one embodiment red and green light components are directed to separate portions of a CCD detector with independent signal processing.

U.S. Pat. No. 6,061,591, to Freitag, entitled, "Arrangement and method for diagnosing malignant tissue by fluorescence observation", discusses a strobed white-light illumination source and laser to stimulate fluorescence. Alternatively, a desired fluorescence spectrum may be isolated and provided from a single lamp, for example, a mercury-vapor xenon lamp. Filter wheels (with red, green and blue filters as well as filters to divide fluorescence into red and green components) and timing requirements are also discussed. Acquisition of white-light images and fluorescence images are performed in sequence, although both may be displayed on the monitor. Various Figures in '591 describe light sources which are similar to those contemplated for the present invention.

The system described in '591 provides the ability to switch back and forth between white light and fluorescence visualization methods, electronically, with display rates up to 10

Hz, or higher. Unlike other prior art (e.g. U.S. Pat. No. 5,647,368 which will be discussed), switching between normal visible light imaging, in full color, and fluorescence imaging is accomplished by an electronic switch rather than by physical optical modulation (switching) by the operator. The '591 patent also discusses a fluorescence excitation light at ultraviolet to deep violet wavelengths placed at the distal end of an endoscope, as well the use of gallium nitride laser diodes and mercury arc lamps for UV illumination of target objects which are also contemplated as illumination sources for various embodiments of the present invention. Also of interest, '591 discusses some limitations of endoscopes and more particularly limitations related to the UV-transmissive properties of optical fibers. Some of these limitations are addressed by co-pending U.S. application Ser. No. 10/226,406 to Ferguson/Zeng, filed approximately Aug. 23, 2002, entitled "Non-coherent fiber optic apparatus and imaging methods".

U.S. Pat. No. 6,019,719, to Schulz, entitled, "Fully auotclavable electronic endoscope", discusses an objective lens, crystal filter, IR filter and CCD chip arranged at the distal end of an endoscope for imaging.

U.S. Pat. No. 5,930,424 to Heimberger, entitled, "Device for connecting a fiber optic cable to the fiber optic connection of an endoscope", discusses various aspects of coupling devices such as light sources to an endoscope.

U.S. Pat. No. 5,926,213 to Hafele, entitled, "Device for correcting the tone of color pictures recorded by a video camera", such as an endoscope camera, is discussed along with a rotary transducer to activate tone correction. Color correction, calibration or normalization is useful for quantization from image data or comparison of images and is considered for various embodiments of the present invention.

U.S. Pat. No. 5,827,190, to Palcic, entitled, "Endoscope having an integrated CCD sensor", discusses illumination light sources and sensors to measure various signals associated with tissue and tissue disease.

U.S. Pat. No. 5,647,368, to Zeng, entitled, "Imaging system for detecting diseased tissue using native fluorescence in the gastrointestinal and respiratory tract", among other things discusses use of a mercury arc lamp to provide for white light and fluorescence imaging with an endoscope to detect and differentiate effects in abnormal or diseased tissue.

U.S. Pat. No. 5,590,660, to MacAulay, entitled, "Apparatus and method for imaging diseased tissue using integrated autofluorescence" discusses light source requirements, optical sensors, and means to provide a background image to normalize the autofluorescence image, for uses such as imaging diseased tissue.

U.S. Pat. No. 5,769,792, to Palcic, entitled, "Endoscopic imaging system for diseased tissue", further discusses light sources and means to extract information from the spectral intensity bands of autofluorescence, which differ in normal and diseased tissue.

Also co-pending U.S. patent application Ser. No. 09/741,731, to Zeng, filed approximately Dec. 19, 2000 and entitled, "Methods and apparatus for fluorescence and reflectance imaging and spectroscopy and for contemporaneous measurements of electromagnetic radiation with multiple measuring devices", (a continuation-in-part of U.S. Publication No. 2002/0103439) discusses contemporaneous methods of providing one mode of imaging and spectroscopy contemporaneously, but multiple imaging and associated spectroscopy modalities in sequential. In the present invention, methods are described to perform multimodal imaging contemporaneously at various desired wavelengths. Unlike Zeng's art, Zeng's present invention does not seek to provide images and measurements of wavelength spectrum, instead it seeks to provide contemporaneous multimodal imaging, where entire images in defined spectrum are detected and acquired for display and/or analysis.

U.S. Pat. No. 5,999,844, to Gombrich, entitled, "Method and apparatus for imaging and sampling diseased tissue using autofluorescence", discusses a plurality of image detectors that receive excitation light as well as depositing biopsies in separate compartments or captive units.

U.S. Pat. No. 6,212,425, to Irion, entitled, "Apparatus for photodynamic diagnosis", discusses endoscopic imaging using a light-induced reaction or intrinsic fluorescence to detect diseased tissue and delivery light for therapeutic use or to stimulate compounds that in turn provide therapy, for example.

U.S. Pat. No. 4,884,133, to Kanno, entitled "Endoscope light source apparatus", discusses light sources, light guides and control of these elements for endoscopic use.

Endoscopes and imaging applications are further discussed in co-pending U.S. application Ser. No. 10/226,406 to Ferguson/Zeng, entitled "Non-coherent fiber optic apparatus and imaging methods", which among other things, discusses apparatus to overcome some existing limitations of fiber optic devices, such as endoscopes.

U.S. Pat. No. 5,749,830 to Kaneko, entitled "Fluorescent endoscope apparatus", discusses use of two light sources, a first (e.g. lamp) for white light and a second (e.g. helium-cadmium laser) for fluorescence, to provide interrogating spectra. Kaneko also employs a filter wheel placed in the pathway of a single detector. For multimodal imaging the filter wheel has a plurality of filters (e.g. three in FIGS. 4a and 5 in FIG. 4b). While they illustrate the display of two imaging modalities (110 of FIG. 7.), they do not discuss simultaneous real-time multimodal imaging. As this art discusses a wide range of issues utilized within the present invention, such as combining light sources, synchronization and filter wheels, (830) is included by reference herein.

Copending application by Zeng et al., filed on May 8, 2003 and entitled "Real time contemporaneous multimodal imaging and spectroscopy uses thereof", is also included by reference.

SUMMARY OF THE INVENTION

Unlike prior art, the present invention employs two excitation-emission pairs to excite and acquire two fluorescence images, simultaneously. In the first pair, blue excitation wavelength band $\lambda 1$-I is used to illuminate tissue to excite fluorescence which provides a spectral emission in the green/red wavelength region $\lambda 1$-E. For this excitation-emission pair ($\lambda 1$-I, $\lambda 1$-E), we have found that diseased tissue such as cancer or pre-cancerous lesions have considerably lower fluorescence signals than healthy tissue.

The second excitation-emission pair is chosen at a wavelength sufficiently distant from the first pair so as to minimize or eliminate spectral overlap and therefore affording simultaneous detection of these two excitation-emission pairs. More particularly, the second illumination spectra $\lambda 2$-I, is selected in the red/NIR band and is used to induce fluorescence emission in the longer red/NIR wavelengths $\lambda 2$-E. Both these illumination bands $\lambda 1$-I, and $\lambda 2$-I produce reflected light which may be exploited alone or in combination with excitation-emission pairs discussed above.

We have discovered particularly useful tissue properties for this second excitation-emission pair ($\lambda 2$-I, $\lambda 2$-E) in diseased tissue such as cancerous or pre-cancerous tissue which unlike the tissue properties discussed in the prior art, exhibits fluorescence intensities which vary in the opposite direction. Typically diseased tissue illuminated at other wavelengths, excites fluorescence at an intensity that is similar or lower than that of normal tissue. Tissue illuminated at λ2-I, excites fluorescence providing intensities that vary in the inverse manner, that is they are higher for diseased tissue than for normal tissue. As will be discussed further, these properties may be uniquely exploited to improve image normalization, sensitivity, and therefore the diagnostic utility of images. To accomplish the object of the present invention, unique optical modulation, detectors and system control are utilized and will also be further discussed, herein.

DETAILED DESCRIPTION OF THE INVENTION

Optical apparatus, such as endoscopy systems, may be described and differentiated in terms of the spectral band(s) used to illuminate tissue and the provisions provided to detect reflected and emitted light which results from the interaction of this light with a target object, such as tissue.

Figure 1A:
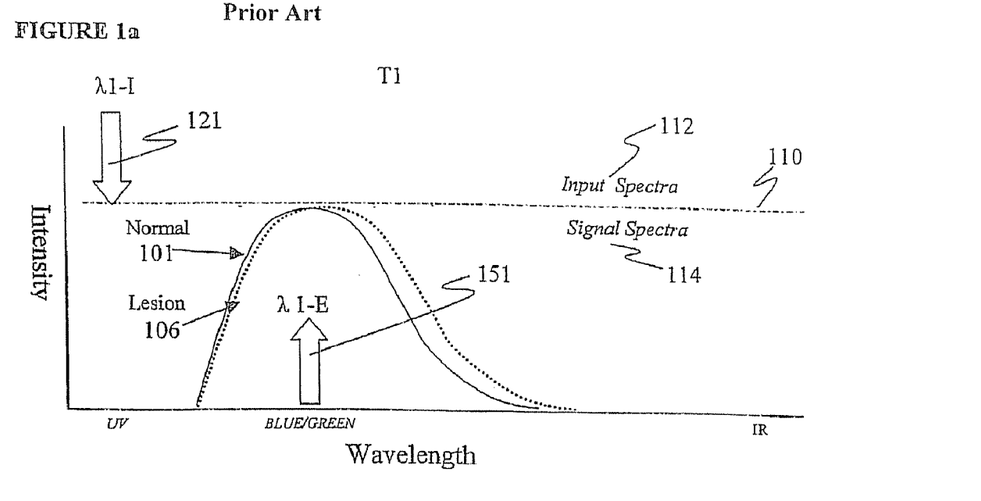
FIG. 1a (prior art) shows use of a single excitation-emission pair to capture an image during a first time interval.
Figure 1B:
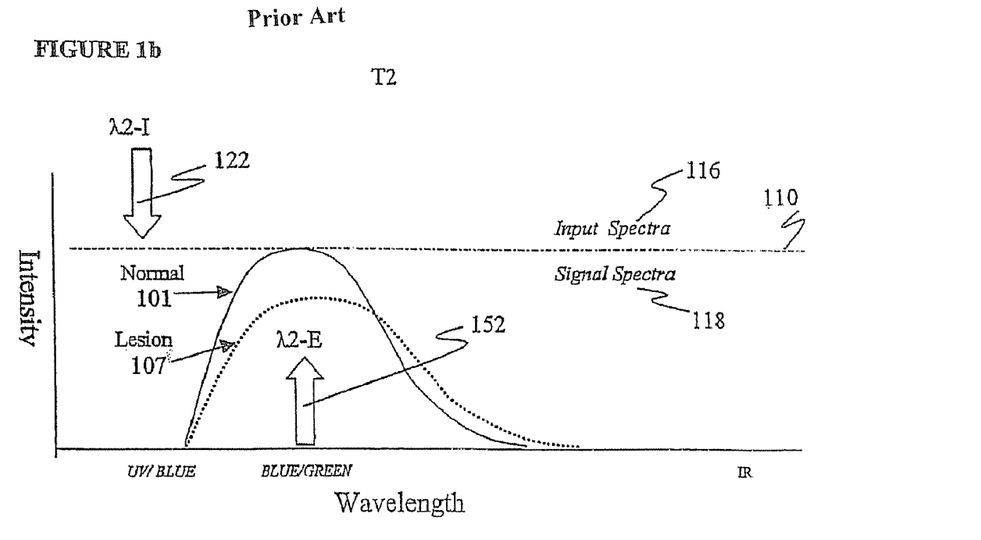
FIG. 1b (prior art) shows use of another single excitation-emission pair used to produce an image for capture during a second time interval.

Accordingly, prior art represented in FIGS. 1a and 1b illustrates a two-channel imaging modality (difference and ratio imaging) for tissue autofluorescence imaging and is thus representative of the endoscopic imaging principles discussed in U.S. Pat. No. 5,413,108 to Alfano entitled, "Method and apparatus for mapping a tissue sample for and distinguishing different regions thereof based on luminescence measurements of cancer-indicative native fluorophor".

As will be discussed further, the two emissions provided in '108 have substantially overlapping spectral bands and therefore the associated spectral images must be captured sequentially, that is, the two emission images are separated in time domain.

FIG. 1a (prior art) is described with input spectra 112 shown above system line 110 with signal or output spectra 114, indicated below system line 110. Accordingly, UV wavelength λ1-I, further identified as arrow 121, is used primarily to excite tissue autofluorescence. The resulting emission occurs in the blue/green wavelength region; a first image of this blue/green emission wavelength λ1-E, further identified as arrow 151 is acquired during time interval T1. Typical emission curves for normal tissue 101, and cancerous tissue 106, are also shown.

At a second time T2, shown in FIG. 1b, a different UV/blue wavelength λ2-I, further identified by legend 122 is used to illuminate tissue. Again, input spectra 116 are shown above line 110 with signal or output spectra 118 shown below. The illumination wavelength 122 is used to excite tissue autofluorescence, which in this instance occurs in the blue/green wavelength region shown as λ2-E, 152. A second image is acquired during this time interval T2.

Ratio and/or differences of the two images may be used to calculate and generate new images for diagnostic purposes. One advantage of such a configuration is that only one image detector is needed to acquire the two images in sequence (a first image during time interval T1 and a second image during time interval T2). A disadvantage of this configuration is imposed because the two images share the same emission wavelength and therefore cannot be separated in space, for example using optical means, and therefore must be separated in time domain (T1 and T2).

This limitation may make the normalization process (image alignment or registration) more difficult for in vivo imaging since the target organ may be moving involuntarily due to breathing and other body activity.

U.S. Pat. No. 6,091,985 to Alfano, entitled, "Detection of cancer and precancerous conditions in tissues and/or cells using native fluorescence excitation spectroscopy" further proposes to chose the excitation wavelength λ1-I so that the emission at λ1-E is indistinguishable between normal tissue and diseased tissue, e.g. cancer and pre-cancer tissues, while λ2-I is so chosen that the emission, λ2-E distinguishes between normal and diseased tissue.

U.S. Pat. No. 6,080,584 to Alfano, entitled "Method and apparatus for detecting the presence of cancerous and precancerous cells in a smear using native fluorescence spectroscopy,", also discusses these principles.

Figure 2:
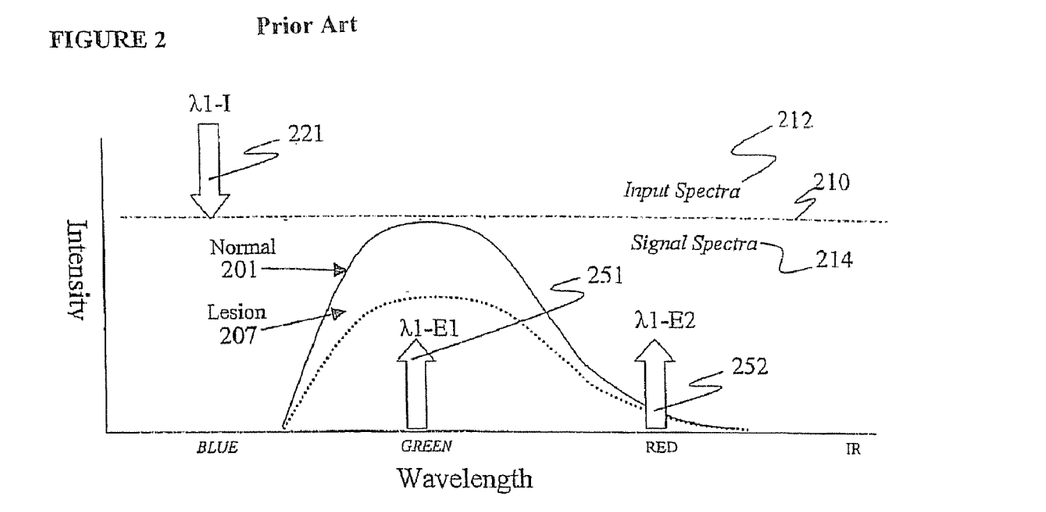
FIG. 2 (prior art) shows use of a single excitation spectral band producing two emission spectral bands for imaging.

FIG. 2 (prior art), is representative of the imaging modality discussed in U.S. Pat. No. 5,507,287 to Palcic entitled "Endoscopic imaging system for diseased tissue" and U.S. Pat. No. 5,769,792 to Palcic, also entitled "Endoscopic imaging system for diseased tissue". Accordingly, the endoscopic imaging system is illustrated with input spectra 212 shown above line 210 with signal output spectra 214, below. In this modality, a single wavelength band λ1-I in the blue region, further identified by legend 221, is used to excite tissue autofluorescence. Two fluorescence images, one in the green wavelength band λ1-E1, and a second in the red wavelength band λ1-E2 are both produced and may therefore be acquired, simultaneously. These two images are then fed to the green and red channels of a video monitor respectively so that a pseudo color image is displayed to aid the detection and delineation of diseased tissue, such as cancer.

Palcic in '287 observes that this modality works best when the green fluorescence intensity is much higher for normal tissue than for cancerous tissue, while the red fluorescence intensity is similar for both normal and cancer tissues. This is further illustrated in the curves 201 (normal) and 207 (diseased or cancerous tissue). In practical use however, the red fluorescence intensity for cancerous tissue is also lower than for normal tissue, but the differences are less than the corresponding differences in the green wavelength band. In other words, the normalization of the green channel image by the red channel image is not particularly good. This may result in normal tissue appearing bright green, while diseased areas may appear reddish when the red fluorescence intensities from normal and diseased tissue are similar. But the diseased tissue area will typically appear dark green when the red fluorescence intensity from diseased tissue is also considerably lower than normal tissue, thus making it more difficult to distinguish a hole or other geometric defect on the imaged tissue surface.

Figure 3:
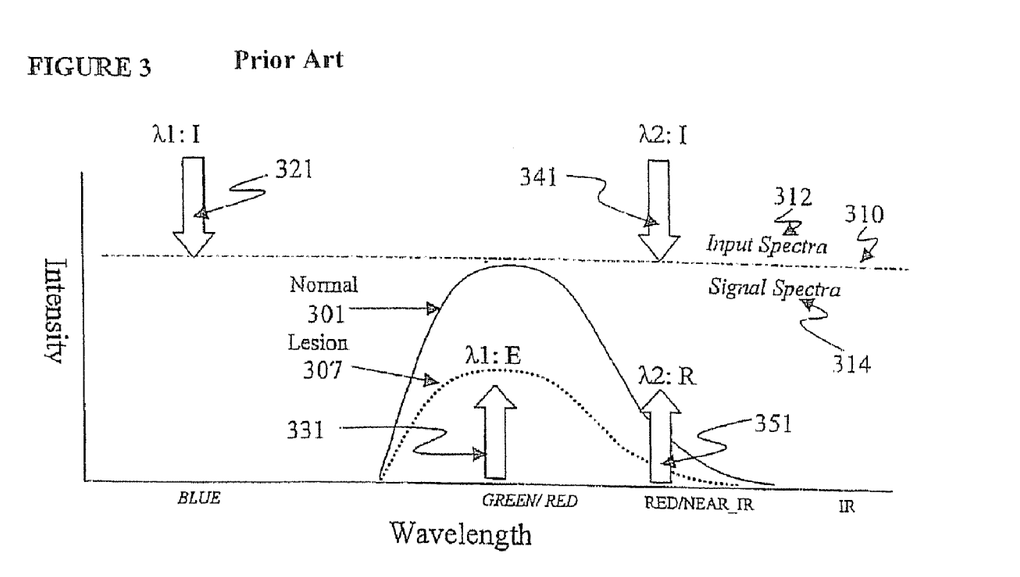
FIG. 3 (prior art) shows the two excitation spectral bands producing a single emission spectral band and a reflectance spectral band at substantially the same wavelength as the second excitation spectral band.

FIG. 3 (prior art) is representative of U.S. Pat. No. 5,590,660, to MacAulay, entitled, "Apparatus and method for imaging diseased tissue using integrated autofluorescence" which also discusses light source requirements, optical sensors, and means to provide a background image to normalize the autofluorescence image. Input spectra 312 are shown above system line 310 with output or signal spectra 314, below.

In this instance, blue excitation band (as in FIG. 2) is used to excite tissue fluorescence so that the integrated fluorescence intensity in the green/red band λ1-E exploits differences between the emission curves 301 for normal tissue and 307 for diseased or cancerous tissue. Again, the intensity for diseased tissue is typically lower than that of normal tissue. A second wavelength λ2-I in the red/NIR band is used to illuminate the tissue and produces back scattered light at this wavelength. In this mode, a fluorescence image is collected in the green/red band (to enhance the difference between normal and diseased tissue), while a reflectance or backscattered light (red/NIR) image is collected, and is used for example to normalize the (green/red) fluorescence image and therefore minimize geometrical and optical non-uniformities. The differences on back scattered red/NIR intensities between normal and diseased tissue are usually much smaller than that of the red fluorescence intensities, therefore, this modality provides improved image normalization over the prior art discussed in association with FIG. 2.

Figure 4:
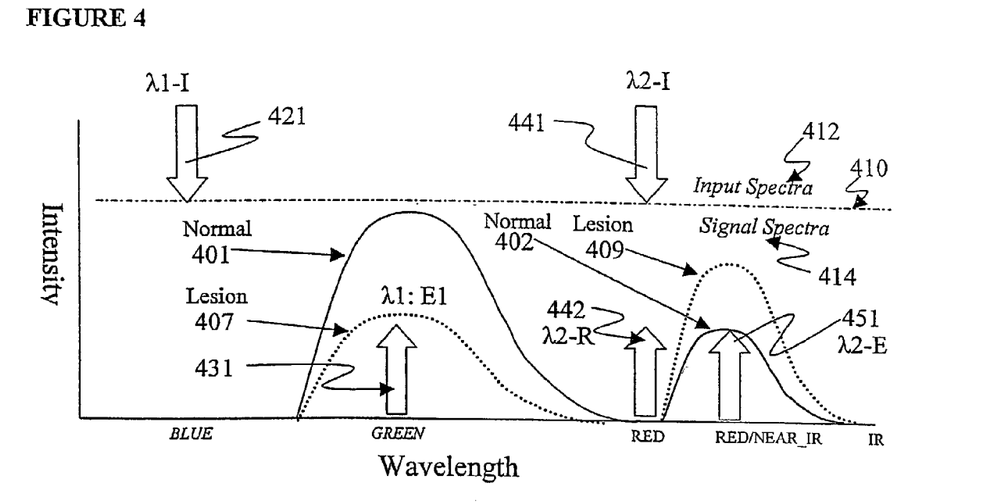
FIG. 4 shows the two excitation-emission pairs of the present invention.

FIG. 4 illustrates an embodiment of the present invention which employs two excitation-emission pairs. Again, input spectra 412 are shown above system line 410 with signal or output spectra below. Input illumination spectra such as λ1-I and λ2-I are used to simultaneously excite tissue emissions providing the corresponding emission pairs λ1-E and λ2-E allowing the two fluorescence images to be acquired simultaneously. In the first pair, blue excitation wavelength band λ1-I is used to excite the tissue to fluoresce in the green/red wavelength region λ1-E. For this excitation-emission pair (λ1-I, λ1-E), we have found that cancer or pre-cancer tissues have considerably lower fluorescence signals than the normal tissue. This is further illustrated by representative tissue emissions curves 401 for normal tissue and 407 for diseased (cancerous tissue). The second excitation-emission pair (λ2-I, λ2-E) is chosen far enough away so as to reduce or eliminate interference (spectral overlap) to allow simultaneous detection of the fluorescence images. More particularly, tissue is illuminated (excited) using red/NIR wavelength λ2-I to induce a fluorescence emission in the longer red/NIR wavelengths λ2-E. For this second excitation-emission pair (λ2-I, λ2-E), we find that cancer or pre-cancer tissues have considerably higher fluorescence signals than the normal tissue.

A unique hardware configuration is used so that tissue may be illuminated at λ1-I and λ2-I, simultaneously and the resulting fluorescence images (at λ1-E and λ2-E) may also be acquired, simultaneously. This configuration is further discussed in association with FIGS. 5a and 5b and FIG. 6, to follow. The image at λ2-E normalizes the image at λ1-E for image non-uniformity caused by both geometric factors and the non-uniformity of the illumination beam. The combination of λ1-E image and λ2-E image also provides improved contrast between diseased and normal tissues as compared with the prior art discussed in association with FIGS. 1, 2 and 3 because the fluorescence intensities between normal and diseased tissues, in this instance vary in opposite directions, i.e. in band λ1-E, normal tissue typically has a high intensity than diseased tissue, while in band λ2-E, normal tissue typically has a lower intensity than diseased tissue.

In the prior art discussed in association with FIGS. 1 and 3, one of the two images has similar signal strength between normal and diseased tissues, while the other image has different signal strength. In the prior art discussed in association with FIG. 2, the signal strength for both images decreased from normal tissue to diseased tissue, the contrast between normal and diseased tissue come from the different degree of decreases in the green and red imaging bands.

Figure 5A:
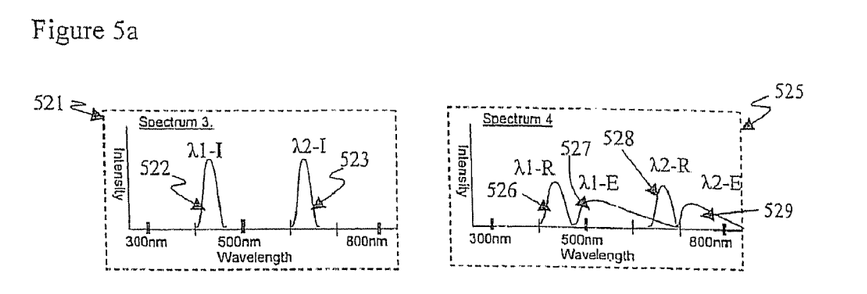
FIG. 5a shows the two excitation-emission pairs of a first embodiment of the present invention.
Figure 5B:
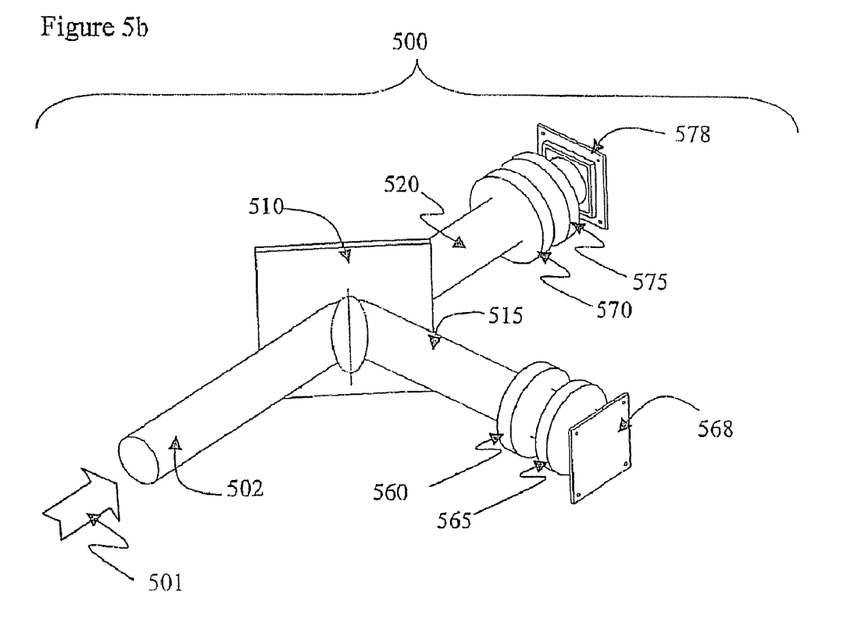
FIG. 5b shows a first embodiment of the present invention for imaging two excitation-emission pairs, simultaneously.

FIGS. 5a and 5b show a hardware embodiment of the present invention to accommodate two excitation-emission pairs. Excitation wavelengths as discussed are used to interrogate tissue, as illustrated in Spectrum 3 521 of FIG. 5a, and to produce emitted and reflected light, as illustrated in Spectrum 4 525 of FIG. 5a. A first excitation wavelength band λ1-I 522, in this instance in the 400 nm to 450 nm band, produces tissue fluorescence λ1-E 527 in the 470 nm to 600 nm spectral band, comprising the first emission-excitation pair. A second excitation wavelength band λ2-I 523, in the near-IR spectral range, in this instance from 610 nm to 680 nm, provides a second fluorescence emission λ2-E 529, which occurs above 650 nm and thus constitutes the second excitation-emission pair. Also as discussed, the reflected light components λ1-R 526 and λ2-R 528 from the first and second excitation spectra are present and may also be detected.

Accordingly, reflected light and the two emitted light spectra (excitation from these two emissions) enter the detector 500 in the direction indicated by arrow 501 in FIG. 5b. Imaging light beam 502 enters the detector 500 and is incident on dichroic mirror 510 set at a 45-degree angle. Dichroic mirror 510 separates imaging light beam 502 into two light beams, beam 515 and beam 520 which are 90 degrees apart from each other. The distance from mirror 510 to each of the two image sensors 578 and 568 is substantially similar.

Beam 515 contains the reflected first excitation light (400 nm to 450 nm) and the first emission light (470 nm to 600 nm). Band pass (BP) filter 560 blocks reflected light and passes the fluorescence light (470 nm to 600 nm). Then lens 565 focuses the filtered light beam on CCD sensor 568 to form a fluorescence image for the first emission band.

Light beam 520 contains the reflected light (610 nm to 640 nm) and fluorescent light above 650 nm from the second excitation. Long pass (LP) filter 570 blocks out light below 650 nm including the reflected light and passes fluorescence light above 650 nm. Lens 575 then focuses the filtered imaging light beam onto CCD sensor 578 to form a second fluorescence image corresponding to the second emission band. In this manner, two excitation-emission images are acquired simultaneously.

The two images as detected by CCD sensors 568 and 578 are then displayed on a monitor as detected. Alternatively, the images can be processed by a computer and displayed on a computer monitor in any number of configurations. Or, the images can be processed by a spectrometer.

Figure 6A:
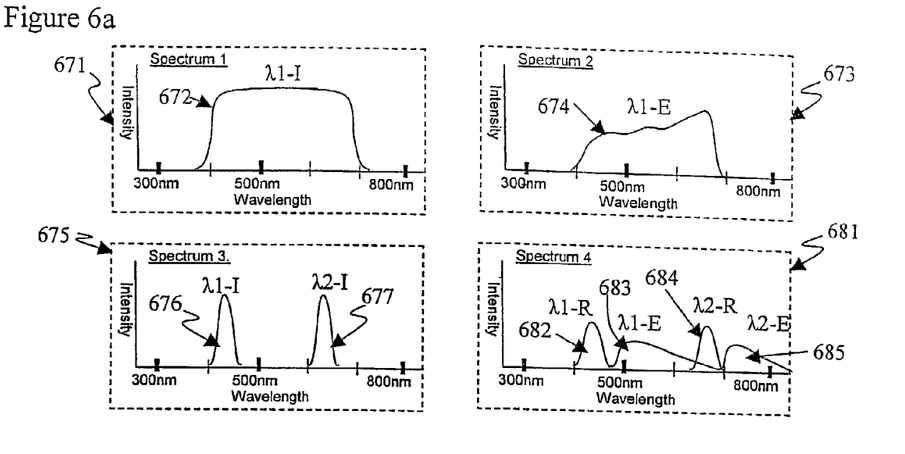
FIG. 6 shows a second embodiment of the present invention for contemporaneous white light imaging and excitation-emission pair imaging in real time, at video rates.
Figure 6B:
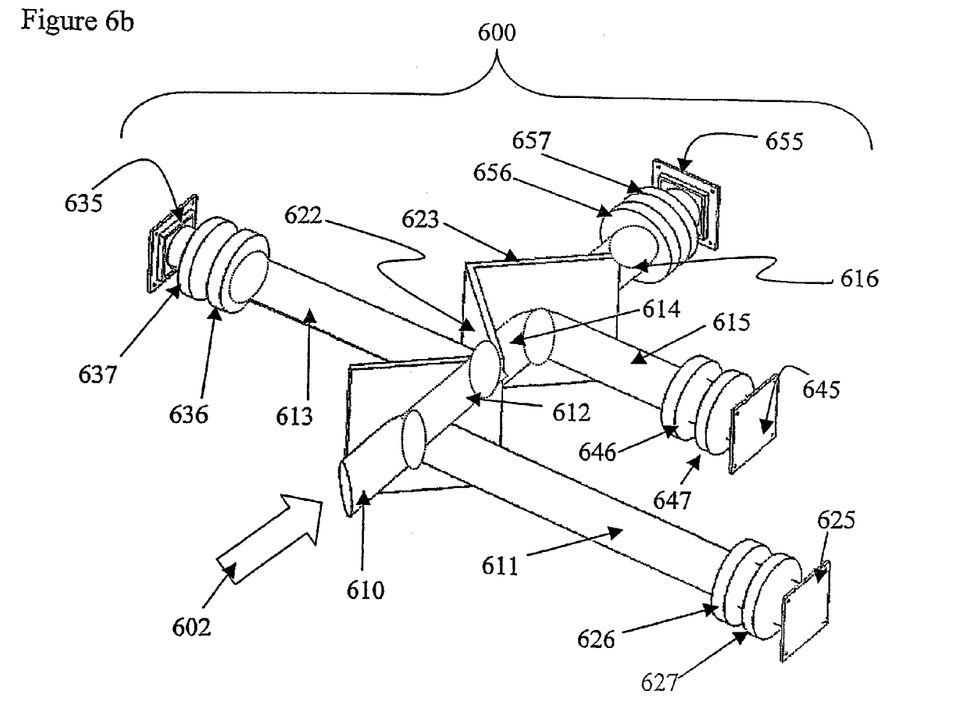

FIG. 6 shows another embodiment of the present invention with a detector configuration that provides for both white light imaging and fluorescence imaging under the illumination of two separate wavelength bands of excitation light. The light 610 reflected and emitted from the target object enters detector 600 as indicated by arrow 602. Compound imaging light beam 610 enters and interacts with a first dichroic mirror 621. This dichroic mirror spits the imaging light beam 610 into two light beams (611 and 612) having altered spectra content. Imaging light beam 611 is directed to filter 626 and lens 627, forming an image on CCD sensor 625. Imaging light 612 passing through mirror 621, interacts with second dichroic mirror 622 where it is again divided into two imaging light beams (613, 614) that carry different spectral content. Imaging light beam 614 then interacts with a third dichroic mirror 623 where it is divided into imaging light beams 615 and 616 having different spectral content. As illustrated and described for light beam 611, imaging beams 613, 615, and 616, with spectral content interact with a respective filter (636, 646, and 656) and lens (637, 647, and 657) to image that spectral content.

Any number and any configuration of dichroic mirrors and filters, both band pass and long and short pass, can be combined to create a desired set of images for the user to observe or analyze. In the illustrated embodiment in FIG. 6, the various dichroic mirrors and filters are configured so that sensor 625 receives blue light, sensor 635 receives green light, sensor 645 receives red light, and sensor 655 receives near-infrared light. The specifications of this particular detector configuration illustrated in FIG. 6 are hereby provided:

dichroic mirror 621—reflects light below 500 nm, transmits light above 500 nm dichroic mirror 622—reflects light below 600 nm, transmits light above 600 nm dichroic mirror 623—reflects light below 700 nm, transmits light above 700 nm BP filter 626—transmitting light from 400 nm to 500 nm, blocking all other wavelengths BP filter 636—transmitting light from 500 nm to 600 nm, blocking all other wavelengths BP filter 646—transmitting light from 600 nm to 700 nm, blocking all other wavelengths LP filter 656—transmitting light above 700 nm, blocking light below 700 nm Lenses 627, 637, 647, and 657 are focus lenses that focus spectral images on CCD image sensors 625, 635, 645, and 655, respectively.

For fluorescence imaging in the apparatus illustrated in FIG. 6, tissue is illuminated by, for example, a first excitation wavelength band $\lambda 1$-I 676 (e.g. 400 nm to 450 nm) and a second excitation wavelength band $\lambda 2$-I 677 (e.g. 620 nm to 680 nm), as illustrated in Spectrum 3 675, which induce tissue fluorescence to produce corresponding emissions: a first fluorescence emission $\lambda 1$-E 683 (e.g. 470 nm to 700 nm) and a second fluorescence emission $\lambda 2$-E 685 (e.g. above 700 nm). The light signals collected by the endoscope include reflected or backscattered light $\lambda 1$-R 682 and $\lambda 2$-R 684 substantially the same as the illumination spectra (e.g. 400 nm to 450 nm and 620 nm to 680 nm) as well as the two tissue fluorescence emissions $\lambda 1$-E 683 and $\lambda 2$-E 685.

Sensor 635 forms the first fluorescence image in the green channel (fluorescence light from 500 nm to 600 nm), and sensor 655 forms the second fluorescence image in the NIR channel using fluorescence light above 700 nm. The blue(B) CCD sensor 625 and red(R) CCD sensor 645 channel are off at this time (imaging fluorescence only) and do not acquire images.

When performing white reflectance imaging in the same apparatus illustrated in FIG. 6, the tissue is illuminated by broadband light from 400 nm to 700 nm, $\lambda 1$-I 672, as illustrated in spectrum 1 671. In this case the light collected by the endoscope consists of only reflected light $\lambda 1$-E 674 from the tissue in this range (400 nm to 700 nm), as illustrated in Spectrum 2 673 (attenuated to some extent, primarily due to absorption). The respective CCD sensors 625 (B), 635 (G), and 645 (R) capture three images in comprising RGB bands: B (e.g. 400-500 nm), G (e.g. 500-600 nm), and R (e.g. 600-700 nm). The NIR CCD sensor 655 is turned off and thus does not capture an image at this time.

The three images as detected by the CCD sensors illustrated in FIG. 6 are then displayed on a monitor as detected. Alternatively, the images can be processed by a computer and displayed on a computer monitor in any number of configurations.

Also, the white light and excitation light can be optically modulated to provide real-time, multimodal imaging simultaneously, as described in copending application entitled Real-time Contemporaneous Multimodal Imaging and Spectroscopy Uses Therefore", filed on May 8, 2003.

Excitation light used in the present invention can be generated by a laser, a light-emitting diode, or other means of providing excitation light, with or without optical modulators.

I claim:

1. An apparatus for fluorescence imaging of a target object that is normal or is diseased, comprising:
    means to illuminate the target object with light in a first excitation wavelength region to excite a first fluorescence emission, said first excitation wavelength region being selected to excite said first fluorescence emission at an intensity greater for the target object that is normal than for the target object that is diseased;
    means to acquire said first fluorescence emission;
    means to simultaneously illuminate said target object with light in a second excitation wavelength region to excite a second fluorescence emission, said second excitation wavelength region being selected to excite said second fluorescence emission at an intensity lower for the target object that is normal than an intensity for the target object that is diseased; and
    means to acquire said second fluorescence emission.

2. The apparatus of claim 1, further comprising means to display said first fluorescence emission and said second fluorescence emission.

3. The apparatus of claim 1, whereby said first excitation wavelength region and said second excitation wavelength region are selected to reduce spectral overlap between said first fluorescence emission and said second fluorescence emission.

4. The apparatus of claim 1, wherein said first excitation wavelength region is in the blue region of the electromagnetic spectrum.

5. The apparatus of claim 4, wherein said first excitation wavelength region is in a spectral range of 400 to 450 nm.

6. The apparatus of claim 1, wherein said second excitation wavelength is in the red/near-infrared region of the electromagnetic spectrum.

7. The apparatus of claim 6, wherein said second excitation wavelength is in a spectral range of 610 to 680 nm.

8. The apparatus of claim 1, wherein said first excitation wavelength region is in the blue region of the electromagnetic spectrum and said second excitation wavelength is in the red/near-infrared region of said electromagnetic spectrum.

9. The apparatus of claim 8, wherein said first excitation wavelength region is in a spectral range of 400 to 450 nm.

10. The apparatus of claim 8, wherein said first excitation wavelength region is in a spectral range of 400 to 450 nm and said second excitation wavelength is in a spectral range of 610 to 680 nm.

11. The apparatus of claim 1, further comprising means to use said second fluorescence emission to normalize said first fluorescence emission.

12. The apparatus of claim 1, further comprising an endoscope.

13. The apparatus of claim 1, wherein
said means to illuminate the target object with light in a first excitation wavelength region produces a first reflection in said first excitation wavelength region;
said means to illuminate the target object with light in a second excitation wavelength region produces a second reflection in said second excitation wavelength region; and
said apparatus further comprises:
a detector, comprising:
a dichroic mirror to separate said first fluorescence emission, said second fluorescence emission, said first reflection, and said second reflection, into a first beam comprising said first fluorescence emission and said first reflection, and a second beam comprising said second fluorescence emission and said second reflection;
a first band pass filter to remove said first reflection from said first beam;
a second band pass filter to remove said second reflection from said second beam;
a first lens to focus said first beam onto a first sensor to form a first image; and
a second lens to focus said second beam onto a second sensor to form a second image.

14. The apparatus of claim 13, further comprising an endoscope.

15. The apparatus of claim 13, further comprising an optical modulator.

16. The apparatus of claim 1, further comprising:
a detector to acquire and separate said first fluorescence emission and said second fluorescence emission;
a first lens to focus said first fluorescence emission on a first sensor to form a first image; and
a second lens to focus said second fluorescence emission on a second sensor to form a second image.

17. The apparatus of claim 16, further comprising an endoscope.

18. The apparatus of claim 16, further comprising an optical modulator.

19. A method of fluorescence imaging of a target object that is normal or is diseased, comprising:
selecting a first excitation wavelength region to excite a first fluorescence emission from the target object at an intensity greater for the target object that is normal than for the target object that is diseased;
selecting a second excitation wavelength region to excite a second fluorescence emission from the target object at an intensity lower for the target object that is normal than for the target object that is diseased;
illuminating the target object with light in said first excitation wavelength region;
acquiring said first fluorescence emission;
simultaneously illuminating said target object with light in said second excitation wavelength region; and
acquiring said second fluorescence emission.

20. The method of claim 19, further comprising displaying said first fluorescence emission and said second fluorescence emission.

21. The method of claim 19, further comprising selecting said first excitation wavelength region and said second excitation wavelength region to reduce spectral overlap between said first fluorescence emission and said second fluorescence emission.

22. The method of claim 19, further comprising selecting said first excitation wavelength region in the blue region of the electromagnetic spectrum.

23. The method of claim 22, wherein said first excitation wavelength region is in a spectral range of 400 to 450 nm.

24. The method of claim 19, further comprising selecting said second excitation wavelength in the red/near-infrared region of the electromagnetic spectrum.

25. The method of claim 24, wherein said second excitation wavelength region is in a spectral range of 610 to 680 nm.

26. The method of claim 19, further comprising selecting said first excitation wavelength region in the blue region of the electromagnetic spectrum and said second excitation wavelength in the red/near-infrared region of said electromagnetic spectrum.

27. The method of claim 26, wherein said first excitation wavelength region is in a spectral range of 400 to 450 nm and said second excitation wavelength region is in a spectral range of 610 to 680 nm.

28. The method of claim 19, further comprising using said second fluorescence emission to normalize said first fluorescence emission.

29. The method of claim 19, further comprising:
producing a first reflection in said first excitation wavelength;
producing a second reflection in said second excitation wavelength;
separating said first fluorescence emission, said second fluorescence emission, said first reflection, and said second reflection into a first beam comprising said first fluorescence emission and said first reflection, and a second beam comprising said second fluorescence emission and said second reflection;
removing said first reflection from said first beam;
removing said second reflection from said second beam;
forming a first image from said first beam; and
forming a second image from said second beam.

30. The method of claim 19, further comprising:
separating said first fluorescence emission and said second fluorescence emission;
forming a first image from said first fluorescence emission; and
forming a second image from said second fluorescence emission.

* * * * *